(12) United States Patent
Chen et al.

(10) Patent No.: US 8,765,421 B2
(45) Date of Patent: Jul. 1, 2014

(54) METHOD FOR PRODUCING COENZYME Q10 BY FERMENTATION USING STOCK CULTURE FROM SOLID PHASE FERMENTATION

(75) Inventors: Jinqing Chen, Xiamen (CN); Dajun Chen, Xiamen (CN); Junhuang Chen, Xiamen (CN); Meiqiong Wu, Xiamen (CN); Songgang Su, Xiamen (CN); Jianzhong Huang, Xiamen (CN); Yi Zheng, Xiamen (CN)

(73) Assignee: Xiamen Kingdomway Group Company, Xiamen, Fujian (CN)

( * ) Notice: Subject to any disclaimer, the term of this patent is extended or adjusted under 35 U.S.C. 154(b) by 0 days.

(21) Appl. No.: 14/002,199

(22) PCT Filed: Apr. 26, 2011

(86) PCT No.: PCT/CN2011/073287
§ 371 (c)(1),
(2), (4) Date: Aug. 29, 2013

(87) PCT Pub. No.: WO2012/116517
PCT Pub. Date: Sep. 7, 2012

(65) Prior Publication Data
US 2013/0330789 A1  Dec. 12, 2013

(30) Foreign Application Priority Data
Mar. 2, 2011 (CN) .......................... 2011 1 0050366

(51) Int. Cl.
*C12P 7/66* (2006.01)
*C12P 1/04* (2006.01)
*A61K 35/74* (2006.01)
*C12R 1/01* (2006.01)

(52) U.S. Cl.
USPC ........................................ 435/133; 435/170

(58) Field of Classification Search
None
See application file for complete search history.

(56) References Cited

U.S. PATENT DOCUMENTS

2013/0302862 A1* 11/2013 Wu et al. ........................ 435/133

FOREIGN PATENT DOCUMENTS

| CN | 101333509 Y | 12/2008 |
| CN | 101381747 A | 3/2009 |
| CN | 101519681 A | 9/2009 |
| KR | 10-2009-0050409 | 5/2009 |
| WO | WO 2008/100782 A2 | 8/2008 |

OTHER PUBLICATIONS

Zheng et al., "Breeding of photosynthetic bacteria with high yield of coenzyme Q10," Chinese Brewing, May 15, 2008, vol. 9, pp. 83-86.
Yen et al., "Cultivation of *Rhodobacter spaeroides* in the Stirred Bioreactor with Different Feeding Strategies for CoQ10 Production," Applied Biochemistry and Biotechnology, Mar. 10, 2009, vol. 160, pp. 1441-1449.
Tian et al., "Improvement of cultivation medium for enhanced production of coenzyme Q10 by photosynthetic *Rhodospirillum rubrum*," Biochemical Engineering Journal, Jun. 25, 2010, vol. 51, No. 3, pp. 160-166.
P. R. China IPO Search Report for PCT/CN2011/073287.

* cited by examiner

*Primary Examiner* — Suzanne M Noakes
*Assistant Examiner* — Gerard Lacourciere
(74) *Attorney, Agent, or Firm* — RatnerPrestia

(57) ABSTRACT

A method for producing coenzyme Q10 by using stock culture from solid phase fermentation. The strain used in this method is *Rhodobacter sphaeroides*. Strain passaging is carried out by culturing in a slant medium. After steam cooking and air drying, solid medium is subpackaged and sterilized, wherein said solid medium includes solid components and liquid components. The fresh culture of *Rhodobacter sphaeroides* on the slant medium is added with sterile water, and the resultant bacterial suspension is added into the solid medium, cultured and used as stock culture for primary fermentation. The method of the present invention can enhance the fermentation level of coenzyme Q10, reduce the cascades of fermentation, shorten production cycle, simplify production processes, and lower production cost.

9 Claims, No Drawings

METHOD FOR PRODUCING COENZYME Q10 BY FERMENTATION USING STOCK CULTURE FROM SOLID PHASE FERMENTATION

CROSS REFERENCE TO RELATED APPLICATIONS

This application is the U.S. National Phase Application of PCT/CN2011/073287, filed Apr. 26, 2011, which claims priority to Chinese Patent Application No. 201110050366.6, filed Mar. 2, 2011, the contents of such applications being incorporated by reference herein.

TECHNICAL FIELD

The invention relates to a fermentation method using stock culture from solid phase fermentation, in particular, a new method for producing coenzyme Q10 by fermentation using stock culture from solid phase fermentation.

BACKGROUND

Coenzyme Q10 (2,3-dimethoxy-5-methyl-6-decaprenyl-1,4-benzoquinone, CoQ10), also named as ubiquinone or ubidecarenone, exists widely in animals, plants and microorganisms, and is an essential hydrogen carrier in respiratory chain of biological cells. Coenzyme Q10 is an important biochemical medicament, and recently has been widely applied in the treatment of various diseases such as cardiovascular diseases, diabetes, cancers, acute and chronic hepatitis, and Parkinson's Disease. In addition, coenzyme Q10 also exhibits a significant effect on the treatment of scurvy, duodenal ulcer and necrotic periodontitis, as well as on the enhancement of the function and secretion of pancreas. Meanwhile, coenzyme Q10 also has an anti-aging effect, and is widely applied in the fields of cosmetics and health products.

There are mainly three kinds of methods for producing coenzyme Q10, namely, i) extraction from animal or plant tissues, ii) chemical synthesis, and iii) fermentation using microorganisms. In the method of extraction from animal or plant tissues, due to low content of animal coenzyme Q10, complicated chemical components, and the limitation of raw materials and sources, the product cost and price are high, and the industrial production is limited to some extent. Chemical synthesis methods are relatively mature technically, but the products are mixtures of cis-isomers and trans-isomers and have low biological activity, and the production cost is high. Therefore, chemical synthesis methods are limited in industrial production. Fermentation methods using microorganisms have become the most prospective methods for producing coenzyme Q10 for the following reasons: raw materials are cheap and abundant; processes for isolation of products are relatively simple; the products are natural products, without the problems generated by isomers; the products have good biological activity and are capable of being absorbed easily in human bodies; and the production in an industrial scale can be accomplished by using fermentation tanks.

During fermentation using microorganisms, seed incubation is the first step for fermentation production, and the quality of seed liquid plays a key role in fermentation production. Seeds with good quality may shorten the fermentation period, stabilize yield and quality, and enhance utilization of devices. Therefore, seed incubation is essential for the production of coenzyme Q10 by fermentation. Currently, the general processes for producing coenzyme Q10 by fermentation using stock culture are as follows: culture in a slant medium→preparation of stock culture→primary enlargement culture→secondary enlargement culture→tertiary enlargement culture (if necessary)→fermentation. In most of the processes, stock culture are cultured by liquid phase fermentation.

Chinese Patent No. CN101519681, which is incorporated by reference, discloses a method for producing coenzyme Q10 by fermentation, wherein the quality of coenzyme Q10 produced thereby is maintained. In this method, the initial metabolic reaction is modulated in a feedback manner, depending on the synthetic rate and the content of the main side-product (i.e., 5-demethoxy coenzyme Q10) during metabolism of coenzyme Q10-producing bacteria, and has a rate-limiting effect on synthetic metabolism, so as to modulate the accumulation of the product of interest (i.e., coenzyme Q10) in cells in a feedback manner. By optimization of the concentration of the main substrates in the fermentation formulation and by optimized modulation of stirring rate during fermentation, the fermentation level of coenzyme Q10 is greatly enhanced, and the fermentation level of coenzyme Q10 can be enhanced to 3000 u/ml or more; and the determination of the optimized timing of discharging into the fermentation tanks improves time availability for producing coenzyme Q10 in cells, reduces fermentation cost, and greatly reduces the consumption of raw materials for fermentation.

SUMMARY OF THE INVENTION

To overcome the disadvantages of fermentation production of coenzyme Q10 using stock culture in the prior art, an aspect of the invention provides a method for producing coenzyme Q10 by fermentation using stock culture from solid phase fermentation, which can improve productivity.

The bacterial strain used in the invention is *Rhodobacter sphaeroides* strain JDW-610, which was deposited in China General Microbiological Culture Collection Center (CGMCC) on Dec. 21, 2010, with an accession number of CGMCC No. 4497.

The method of the invention comprises the following steps:
1) passaging the strain by culturing in a slant medium;
2) preparing a solid medium, wherein the solid medium is steam-cooked and dried in air, subpackaged and sterilized, wherein said solid medium comprises solid components and liquid components; and
3) culturing stock culture from solid phase fermentation, wherein a bacterial suspension is prepared by adding the culture of fresh *Rhodobacter sphaeroides* in the slant medium into sterile water, the suspension is added into the solid medium, and then cultured and used as stock culture for primary fermentation.

In step 1), the slant medium may be comprised of: glucose 10 g/L, yeast extract paste 5 g/L, peptone 5 g/L, sodium chloride 5 g/L, ammonium sulfate 0.5 g/L, vitamin $B_1$ 1 µg/L, vitamin K 1 µg/L, vitamin A 1.5 µg/L, $Na_2MoO_4 \cdot 2H_2O$ 0.8 µg/L, $ZnSO_4 \cdot 7H_2O$ 1.2 µg/L, $KNO_3$ 0.33 µg/L, NaBr 0.44 µg/L, agar 20 g/L, pH 7.2; the culture condition may be: sterilization temperature of 121° C., sterilization time of 25 min, culture at 30° C. in dark for 24 h, stored at 4° C. for further use, activated prior to use.

In step 2), the formulation of the solid components may be comprised of: bran, rice, and millet in a ratio of 25:25:50 by mass; the formulation of the liquid components may be comprised of: glucose 10 g/L, yeast extract paste 5 g/L, peptone 5 g/L, sodium chloride 5 g/L, calcium chloride 2 g/L, ammonium sulfate 0.5 g/L, vitamin $B_1$ 1 µg/L, vitamin K 1 µg/L, vitamin A 1.5 µg/L, $CuSO_2 \cdot 5H_2O$ 0.6 µg/L, $Na_2MoO_4 \cdot 2H_2O$ 0.8 µg/L, $ZnSO_4 \cdot 7H_2O$ 1.2 µg/L, KNO3 0.33 µg/L, NaBr 0.44 µg/L, pH 7.2; the ratio of the solid components and the liquid components may be 10:7 by mass; the temperature for steam cooking may be 80° C., and the time for steam cooking may be 40 min. The solid medium may be subpackaged into 1000 mL kjeldahl flasks with 200 g per flask, and the sterilization may be carried out at a temperature of 121° C. for 30 min.

In step 3), the culturing may be carried out at 30° C. in dark for 12 h, and continued for another 12 h after shaking homogeneously.

An aspect of the present invention, a process of producing coenzyme Q10 using stock culture from solid phase fermentation is established according to the physiological characteristics of the coenzyme Q10-producing bacteria, with the original fermentation quality of coenzyme Q10 maintained. The process aims at simplifying seed process and enhancing productivity of coenzyme Q10, by carrying out a large number of experiments to optimize the seed process. By optimization of the conditions for seed culture, the invention provides a method for producing coenzyme Q10 by fermentation using stock culture from solid phase fermentation, which finally affects the fermentation and enhances productivity.

The invention employs, for the first time, a new fermentation method of culturing stock culture from solid phase fermentation in the seed incubation process of coenzyme Q10 fermentation, wherein solid materials such as bran, rice and millet are used in place of agar powder to prepare a solid medium. As solid supporters, bran, rice, and millet provide a larger surface area than agar plate, and thus they can provide more seeds in a limited volume. In addition, these solid raw materials comprise a variety of growth factors. Particularly, bran and millet are more abundant in trace nutrients. Therefore, these solid materials are very suitable for seed culture. Meanwhile, stock culture from solid phase fermentation are more convenient for storage and are long-lasting, which is convenient for scheduling fermentation production.

It can be seen that, as compared to liquid phase fermentation, the invention has the following advantages: ① bacterial cells have strong growth activity and good synchronism, can grow quickly after being transferred to a fermentation tank with a short lag phase; ② bacterial cells are in a stable physiological state and retain stable productivity; and ③ the seed incubation process is simplified and the fermentation process is more readily scheduled.

The invention establishes a method for producing coenzyme Q10 by fermentation using stock culture from solid phase fermentation for the first time. The method is applicable in middle-scale and large-scale fermentation, and achieves desirable fermentation effects.

EMBODIMENTS

Example 1

Comparison of Shake-Flask Fermentation of Coenzyme Q10 Using Stock Culture From Liquid Phase Fermentation and Solid Phase Fermentation Flow chart of shake-flask fermentation using stock culture from solid phase fermentation: fresh slant→stock culture from solid phase fermentation→fermentation in a shake flask→extraction of fermentation broth→detection of Q10 titer by HPLC. The procedure was as follows.

The culture on a slant medium and culture of solid stock culture were as described in Summary of the Invention. The prepared solid stock culture was added into 400 mL sterile water, and the lawn on the surface of the solid was washed off with the water and formed a bacterial suspension. The suspension was inoculated with an inoculum size of 10% to the fermentation medium contained in a shake flask, and then the resultant mixture was cultured in dark at 30° C., 200 r/min for 48 h; the fermentation broth was extracted and was detected for titer.

Flow chart of shake-flask fermentation using stock culture from liquid phase fermentation: fresh slant→primary stock culture by liquid phase fermentation→secondary fermentation→extraction of fermentation broth→detection of fermentation level by HPLC. The procedure was as follows.

The slant bacterial suspension was prepared as described in Summary of the Invention. The prepared slant bacterial suspension was inoculated with an inoculum size of 1.2% to a primary seed medium contained in a shake flask. The resultant mixture was cultured in dark at 30° C., 200 r/min for 24 h. Then, the primary seeds in the shake flask were inoculated with an inoculums size of 10% to a secondary fermentation medium contained in a shake flask, and the resultant mixture was cultured in dark at 30° C., 200 r/min for 48 h. The fermentation broth was extracted and detected for titer.

The experimental results of shake-flask fermentation using stock culture from liquid phase fermentation and solid phase fermentation were compared and shown in Table 1. The results showed that the stock culture from solid phase fermentation has the following advantages:

① strains are larger in size and are plumper;
② strains have strong activity and strain concentration is higher; and
③ seed process is simplified.

TABLE 1

Results of shake-flask fermentation using stock culture from liquid phase fermentation and solid phase fermentation

| | | Detection of the final fermentation broth | | |
| --- | --- | --- | --- | --- |
| Seed process | OD | Wet weight (g/5 mL) | microscopic examination of bacterial cells | Titer (IU/mL) |
| Liquid seed | 0.190 | 0.310 | circular, small | 73.46 |
| Liquid seed | 0.198 | 0.317 | circular, small | 76.25 |
| Liquid seed | 0.187 | 0.306 | circular, small | 69.61 |
| Solid seed | 0.211 | 0.324 | circular, plump and large | 87.98 |
| Solid seed | 0.227 | 0.336 | circular, plump and large | 93.38 |
| Solid seed | 0.224 | 0.334 | circular, plump and large | 89.48 |

Example 2

Comparison of Fermentation Production of Coenzyme Q10 Using Stock Culture From Liquid Phase Fermentation and Solid Phase Fermentation in a 100 L Laboratory Tank Flow chart of fermentation of stock culture from solid phase fermentation in a laboratory scale: fresh slant→stock culture from solid phase fermentation→a 30 L seed tank→a 100 L fermentation tank→extraction of fermentation broth→detection of fermentation level by HPLC. The procedure was as follows.

The fresh slant and stock culture from solid phase fermentation bacterial suspension was prepared as described above. The prepared stock culture from solid phase fermentation bacterial suspension was inoculated with an inoculum size of 1.2% to a 30 L seed tank to a final volume of 15 L. The resultant seed liquor was cultured in dark at 30° C., pH 5.5~5.8, 200 r/min, 0.02~0.04 MPa, ventilatory capacity of 0.8~1.1 m$^3$/h, for 30 h. The seed liquor was inoculated with an inoculum size of 10% to a 100 L fermentation tank to a final volume of 60 L, and then the resultant mixture was cultured in dark at 32° C., pH 5.5~5.8, 200 r/min, 0.02~0.05 MPa, ventilatory capacity of 1.8~2.8 m$^3$/h for 88 h until the fermentation was finished. Samples were taken out to detect titer every 8 h after fermentation for 40 h.

Flow chart of fermentation of stock culture from liquid phase fermentation in a laboratory scale: fresh slant→stock culture from liquid phase fermentation in a primary shake flask→a 30 L secondary seed tank→a 100 L fermentation tank→extraction of fermentation broth→detection of fermentation level by HPLC. The procedure was as follows.

The slant bacterial suspension was prepared as described above. The prepared slant bacterial suspension was inoculated with an inoculum size of 1% to a stock culture from liquid phase fermentation medium contained in a primary shake flask, and the resultant seed liquor was cultured in dark at 30° C., 200 r/min for 24 h. The seed liquor in the primary shake flask was inoculated with an inoculum size of 1.2% to the secondary seed tank to a final volume of 15 L. Then the resultant mixture was cultured in dark at 30° C., pH 5.5~5.8, 200 r/min, 0.02~0.04 MPa, a ventilatory capacity of 0.8~1.1 $m^3/h$ for 30 h. The secondary seed liquor was inoculated with an inoculum size of 10% to a 100 L fermentation tank to a final volume of 60 L. Then the resultant mixture was cultured in dark at 32° C., pH 5.5~5.8, 200 r/min, 0.02~0.05 MPa, ventilatory capacity of 1.8~2.8 $m^3/h$ for 88 h until the fermentation was finished. Samples were taken out for detection of titer every 8 h after fermentation for 40 h.

During fermentation, feedstock was supplemented twice, at 55 h and 72 h of fermentation, respectively. The feedstock was in such a volume that the fermentation broth had a glucose content of 4 g/L and a pH of 5.5~5.8.

The experimental results of fermentation of stock culture from liquid phase fermentation and solid phase fermentation in a 100 L laboratory tank were compared and shown in Table 2. The results showed that the stock culture from solid phase fermentation has the following advantages:

① bacterial cells have strong growth activity and good synchronism, can grow quickly after transferring the seeds to the fermentation tank, with a short lag phase;

② bacterial cells are in a stable physiological state and retain stable productivity;

③ seed incubation process is simplified and the fermentation period is shortened.

TABLE 2

Results of fermentation of stock culture by liquid phase fermentation and solid phase fermentation in a 100 L laboratory tank

| | | Time (h) | | | | | | |
|---|---|---|---|---|---|---|---|---|
| | | 40 | 48 | 56 | 64 | 72 | 80 | 88 |
| Liquid seed | titer (IU/mL) | 963 | 1197 | 1499 | 1817 | 2056 | 2217 | 2345 |
| Solid seed | titer (IU/mL) | 1102 | 1614 | 1946 | 2362 | 2654 | 3009 | 3224 |

Example 3

Comparison of Fermentation Production of Coenzyme Q10 Using Stock Culture From Liquid Phase Fermentation and Solid Phase Fermentation in a Middle-Scale 1T Fermentation Tank Flow chart of the fermentation using stock culture from solid phase fermentation in a middle-scale 1T fermentation tank: fresh slant→stock culture from solid phase fermentation→a 100 L fermentation tank→a 1T fermentation tank→extraction of the fermentation broth→detection of fermentation level by HPLC. The procedure was as follows.

(1) The bacterial strain, strain passage, and stock culture from solid phase fermentation bacterial suspensions were prepared as described in Summary of the Invention.

(2) A secondary seed tank (100 L): the two prepared stock culture from solid phase fermentation bacterial suspension were inoculated with an inoculum size of 1.2% to the medium contained in a secondary seed tank to a final volume of 60 L. Then the resultant mixture was cultured in dark at 30° C., pH 5.8, 200 r/min, 0.02~0.04 MPa, ventilatory capacity of 1.8~2.8 $m^3/h$, for 30 h;

(3) A third level fermentation tank (1T): the secondary seed liquor was inoculated with an inoculum size of 10% to 1T tertiary fermentation medium to a final volume of 600 L. Then the resultant mixture was cultured in dark at 32° C., pH 5.5~5.8, 200 r/min, 0.02~0.05 MPa, ventilatory capacity of 18~28 $m^3/h$ for 88 h, and discharged from the fermentation tank, wherein during fermentation, glucose solution and aqueous ammonia were fed to control the indexes such as total sugar and reducing sugar, and pH within a given range.

The feedstock was supplemented as described above.

The experimental results of fermentation of coenzyme Q10 using stock culture from liquid phase fermentation and solid phase fermentation in a scale 1T fermentation tank were compared and shown in Table 3. The results showed that the stock culture from solid phase fermentation has the following advantages:

① bacterial cells have strong growth activity and good synchronism, can grow quickly after transferring them to a fermentation tank, with a short lag phase;

② strains are in a stable physiological state, retain a stable productivity and have a high yield;

③ the seed incubation process is simplified and the production cost is reduced.

Table 3 Fermentation production of coenzyme Q10 in a 1T tank using stock culture from liquid phase fermentation and solid phase fermentation

| | | Time (h) | | | | | | |
|---|---|---|---|---|---|---|---|---|
| | | 40 | 48 | 56 | 64 | 72 | 80 | 88 |
| Liquid seed | titer (IU/mL) | 905 | 1100 | 1329 | 1733 | 1958 | 2119 | 2316 |
| Solid seed | titer (IU/mL) | 1201 | 1810 | 2012 | 2350 | 2655 | 3010 | 3280 |

The formulations of the seed medium and the fermentation medium were as follows.

(1) Seed medium: glucose 15, yeast extract paste 7, peptone 6.5, sodium chloride 6.5, calcium carbonate 5, $CuSO_2.5H_2O$ 0.6 µg, $Na_2MoO_4.2H_2O$ 0.8 µg, $ZnSO_4.7H_2O$ 1.2 µg, $KNO_3$ 0.33 µg, NaBr 0.44 µg, with a final volume of 1 L, pH 5.8, which was sterilized at 121° C. for 30 min.

(2) Fermentation medium: glucose 20, yeast extract paste 10, peptone 10, sodium chloride 10, corn steep powder 40, ammonium sulfate 5, calcium carbonate 5, $CuSO_2.5H_2O$ 1.2 µg, $Na_2MoO_4.2H_2O$ 1.6 µg, $ZnSO_4.7H_2O$ 2.4 µg, $KNO_3$ 0.66 µg, NaBr 0.88 µg, to a final volume of 1 L, pH 5.8, 121° C. 30 min sterilization; glucose solution at a concentration of 40%; aqueous ammonia at a concentration of 28%; wherein glucose solution was sterilized at 118° C. for 25 min.

HPLC conditions for detecting the product of interest, i.e., coenzyme Q10, in the fermentation broth were as follows.

Chromatography column: Hypersil ODS 4.6 mm×150 mm, 5 µm, a stainless steel column;

Detection wavelength: 275 nm;

Mobile phase: absolute alcohol: absolute methanol=35:65;

Flow rate: 1.1 mL/min;

Column temperature: 35° C.

| | | | |
|---|---|---|---|
| 0-1 | PCT/RO/134 (SAFE) INDICATIONS RELATING TO DEPOSITED MICROORGANISM OR OTHER BIOLOGICAL MATERIAL (PCT Rule 13bis) | | |
| 0-1-1 | Software Version | | PCT-SAFE Version 3.51.048.224 MT/FOP 20110101/0.20.5.19 |
| 0-2 | International Application Number | | PCT/CN2011/073287 |
| 0-3 | Applicant's or agent's file reference | | SHXAP33189 |
| 1 | The indications made below relate to the deposited microorganism or other biological material referred to in the description | | |
| 1-1 | page | | 2 |
| 1-2 | line | | 8 |
| 1-3 | IDENTIFICATION OF DEPOSIT | | |
| 1-3-1 | Name of depositary institution | | China General Microbiological Culture Collection Center (CGMCC) |
| 1-3-2 | Address of depositary institution | | Institute of Microbiology, Chinese Academy of Sciences, No. 1, West Beichen Road, Chaoyang District, Beijing 100101, China |
| 1-3-3 | Date of Deposit | | Dec. 21, 2010 |
| 1-3-4 | Accession Number | | CGMCC No. 4497 |
| 1-5 | DESIGNATED STATES FOR WHICH INDICATIONS ARE MADE | | All designated states |
| | For receiving Office use only | | |
| 0-4 | This sheet was received with the international application (yes or no) | | |
| 0-4-1 | Authorized officer | | |
| | For International Bureau use only | | |
| 0-5 | This sheet was received by the International Bureau on: | | |
| 0-5-1 | Authorized officer | | |

The invention claimed is:

1. A method for producing coenzyme Q10 by fermentation using stock culture from solid phase fermentation, wherein, the bacterial strain used is *Rhodobacter sphaeroides*, which was deposited in China General Microbiological Culture Collection Center (CGMCC) on Dec. 21, 2010, with an accession number of CGMCC No. 4497, and the method comprises the following steps:

1) passaging the strain by culturing in a slant medium;
2) preparing a solid medium, wherein the solid medium is steam-cooked and dried in air, subpackaged and sterilized, wherein said solid medium comprises solid components and liquid components; and
3) culturing stock culture from solid phase fermentation, wherein a bacterial suspension is prepared by adding the culture of fresh *Rhodobacter sphaeroides* in the slant medium into sterile water, the suspension is added into the solid medium, and then cultured and used as stock culture for primary fermentation.

2. The method according to claim 1, wherein
in step 1), the formulation of the slant medium is: glucose 10 g/L, yeast extract paste 5 g/L, peptone 5 g/L, sodium chloride 5 g/L, ammonium sulfate 0.5 g/L, vitamin $B_1$ 1 µg/L, vitamin K 1 µg/L, vitamin A 1.5 µg/L, $Na_2MoO_4 \cdot 2H_2O$ 0.8 µg/L, $ZnSO_4 \cdot 7H_2O$ 1.2 µg/L, $KNO_3$ 0.33 µg/L, NaBr 0.44 µg/L, agar 20 g/L, pH 7.2.

3. The method according to claim 1, wherein
in step 1), the culture condition is: sterilization temperature of 121° C., sterilization time of 25 min, culture at 30° C. in dark for 24 h, stored at 4° C. for further use.

4. The method according to claim 1, wherein
in step 2), the formulation of the solid components is comprised of: bran, rice, and millet in a ratio of 25:25:50 by mass.

5. The method according to claim 1, wherein
in step 2), the formulation of the liquid components is comprised of: glucose 10 g/L, yeast extract paste 5 g/L, peptone 5 g/L, sodium chloride 5 g/L, calcium chloride 2 g/L, ammonium sulfate 0.5 g/L, vitamin $B_1$ 1 µg/L, vitamin K 1 µg/L, vitamin A 1.5 µg/L, $CuSO_2 \cdot 5H_2O$ 0.6 µg/L, $Na_2MoO_4 \cdot 2H_2O$ 0.8 µg/L, $ZnSO_4 \cdot 7H_2O$ 1.2 µg/L, $KNO3$ 0.33 µg/L, NaBr 0.44 µg/L, pH 7.2.

6. The method according to claim 1, wherein, in step 2), the ratio of the solid components and the liquid components is 10:7 by mass.

7. The method according to claim 1, wherein, in step 2), the temperature for steam cooking is 80° C., and the time for steam cooking is 40 min.

8. The method according to claim 1, wherein, in step 2), the solid medium is subpackaged into 1000 mL kjeldahl flask with 200 g per flask for subpackage, and the sterilization is carried out at a temperature of 121° C. for 30 min.

9. The method according to claim 1, wherein, in step 3), the culture is carried out at 30° C. in dark for 12 h, and continued for another 12 h after shaking homogeneously.

* * * * *